(12) United States Patent
Bowman et al.

(10) Patent No.: US 11,751,888 B2
(45) Date of Patent: Sep. 12, 2023

(54) SURGICAL INSTRUMENT

(71) Applicant: Smith & Nephew, Inc., Memphis, TN (US)

(72) Inventors: Steven Mark Bowman, Sherborn, MA (US); James J. Kennedy, III, Mont Vernon, NH (US); Sean M. Frick, Somerville, MA (US); Glenn Kenneth Trainer, Somerville, MA (US); Jon B. Taylor, Groton, MA (US); David J. Callaghan, Waltham, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 232 days.

(21) Appl. No.: 17/147,604

(22) Filed: Jan. 13, 2021

(65) Prior Publication Data

US 2021/0137536 A1 May 13, 2021

Related U.S. Application Data

(60) Continuation of application No. 16/409,987, filed on May 13, 2019, now Pat. No. 10,925,620, which is a division of application No. 14/096,660, filed on Dec. 4, 2013, now Pat. No. 10,357,259.

(60) Provisional application No. 61/757,843, filed on Jan. 29, 2013, provisional application No. 61/733,479, filed on Dec. 5, 2012.

(51) Int. Cl.
   *A61B 17/16* (2006.01)
(52) U.S. Cl.
   CPC ...... *A61B 17/1675* (2013.01); *A61B 17/1617* (2013.01)

(58) Field of Classification Search
   CPC ............ A61B 17/1615; A61B 17/1617; A61B 17/1631; A61B 17/1675; A61B 17/1714
   See application file for complete search history.

(56) References Cited

U.S. PATENT DOCUMENTS

| 3,702,611 | A | * | 11/1972 | Fishbein | ............ | A61B 17/1666 |
| | | | | | | 606/81 |
| 4,992,010 | A | * | 2/1991 | Fischer | ............... | B23B 51/0045 |
| | | | | | | 175/286 |
| 5,242,461 | A | * | 9/1993 | Kortenbach | ... | A61B 17/320725 |
| | | | | | | 606/159 |
| 5,817,095 | A | * | 10/1998 | Smith | ................ | A61B 17/1617 |
| | | | | | | 606/79 |
| 10,492,800 | B2 | * | 12/2019 | Papenfuss | .......... | A61B 17/1617 |

(Continued)

*Primary Examiner* — Matthew J Lawson
(74) *Attorney, Agent, or Firm* — Burns & Levinson LLP; Joseph M. Maraia; Marlo Schepper Grolnic

(57) ABSTRACT

A cannulated retrograde reamer is adjustable to create tunnels of multiple different diameters. The cannulated retrograde reamer has a first tubular shaft and a second tubular shaft disposed about the first tubular shaft. A cutting member is pivotably coupled to the distal end of the first tubular shaft. The distal end of the second tubular shaft is configured to engage and disengage the proximal end of the cutting member by the rotation and axial movement of the second tubular shaft relative to the first tubular shaft to open and close the cutting member. The cannulated retrograde reamer substantially reduces the risk of tunnel malposition and/or misalignment, and can be adjusted to create a range of tunnel diameters, thereby allowing inventory levels to be reduced for a surgical case.

9 Claims, 16 Drawing Sheets

(56) References Cited

U.S. PATENT DOCUMENTS

| | | | |
|---|---|---|---|
| 2006/0241629 A1* | 10/2006 | Krebs | A61B 17/1668 606/80 |
| 2007/0276391 A1* | 11/2007 | Graves | A61B 17/1617 606/80 |
| 2010/0249785 A1* | 9/2010 | Betts | A61B 17/320016 606/79 |
| 2011/0251616 A1* | 10/2011 | Osman | A61B 17/1671 606/80 |
| 2014/0207142 A1* | 7/2014 | Takeuchi | A61B 17/16 606/80 |
| 2014/0276844 A1* | 9/2014 | Bourque | A61B 17/1631 606/80 |
| 2016/0038157 A1* | 2/2016 | Mirochinik | A61B 17/1617 606/80 |
| 2020/0170652 A1* | 6/2020 | Kam | A61B 17/1617 |

* cited by examiner

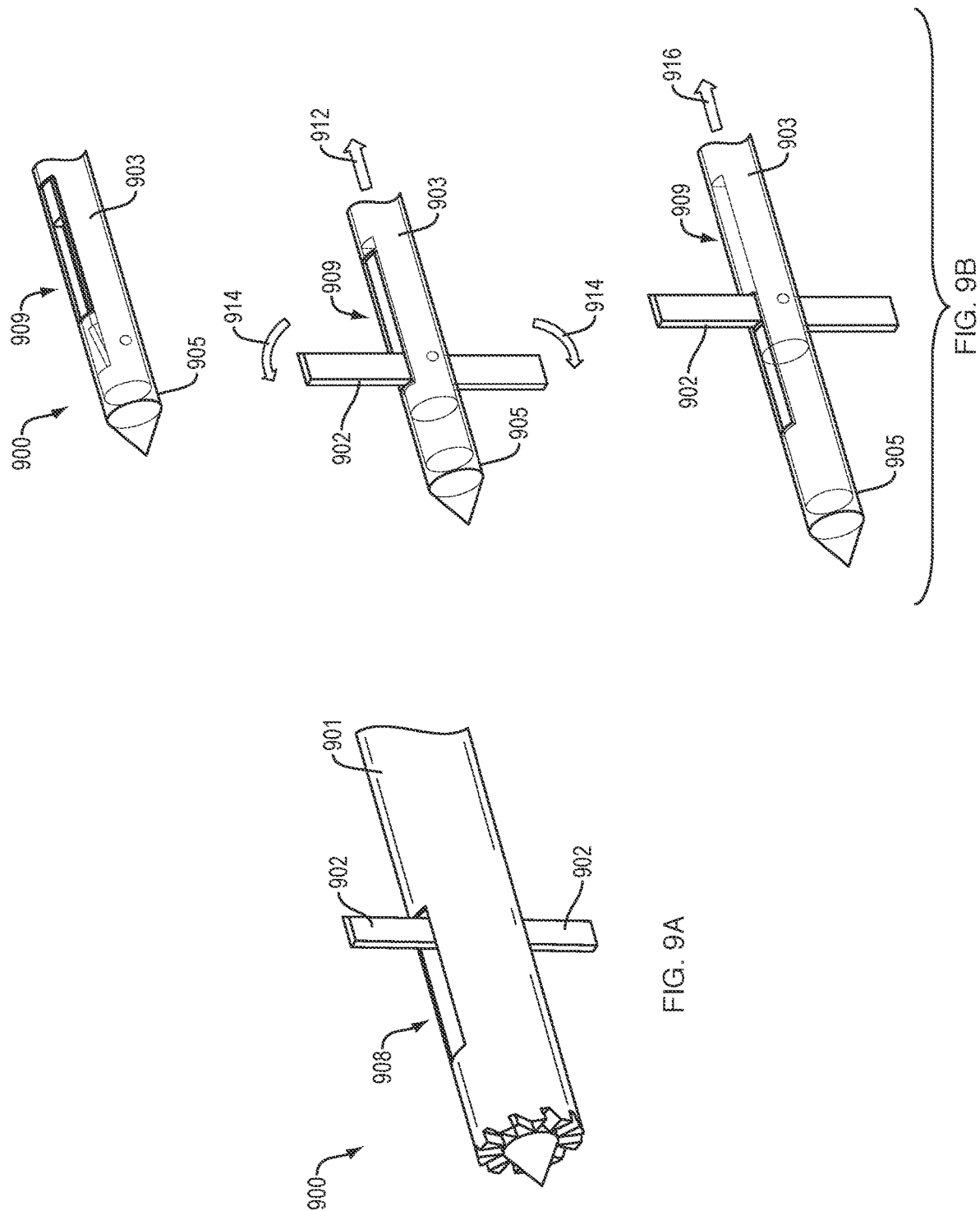

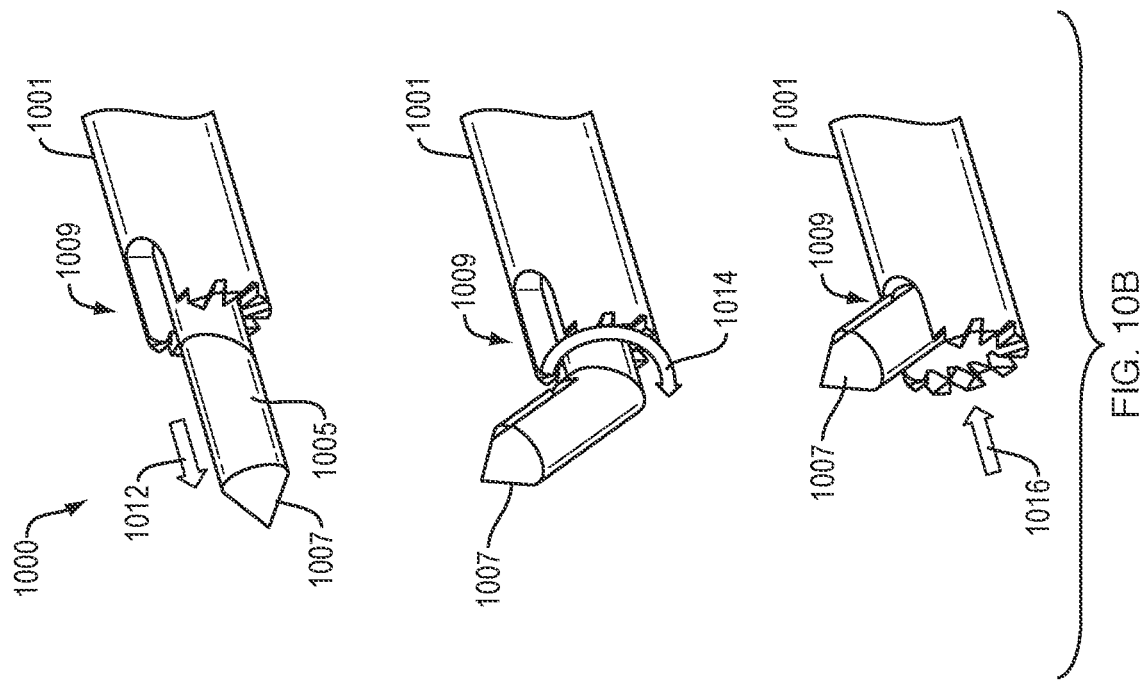
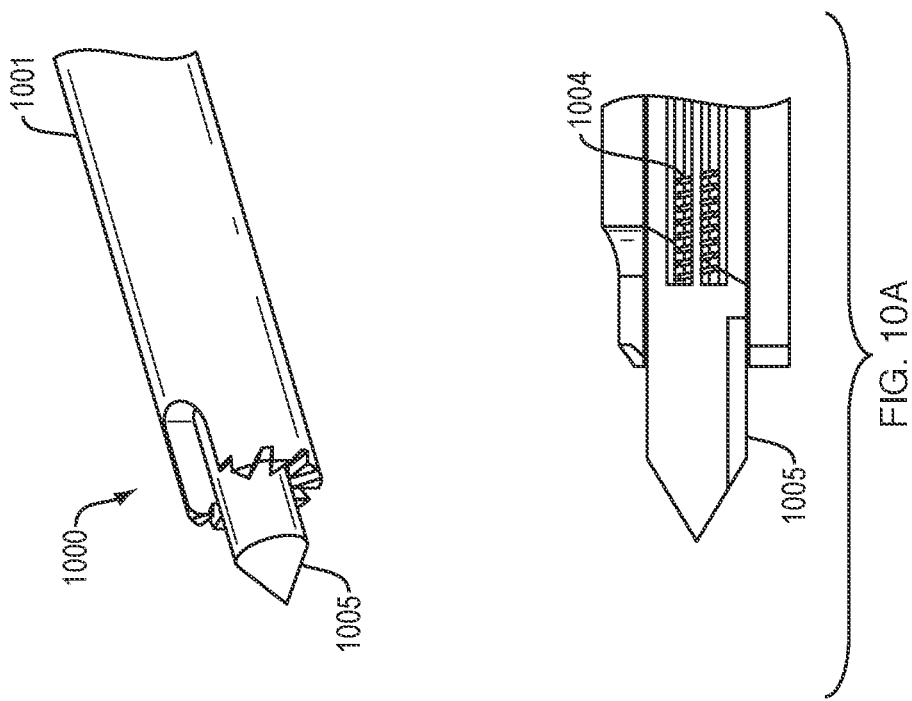

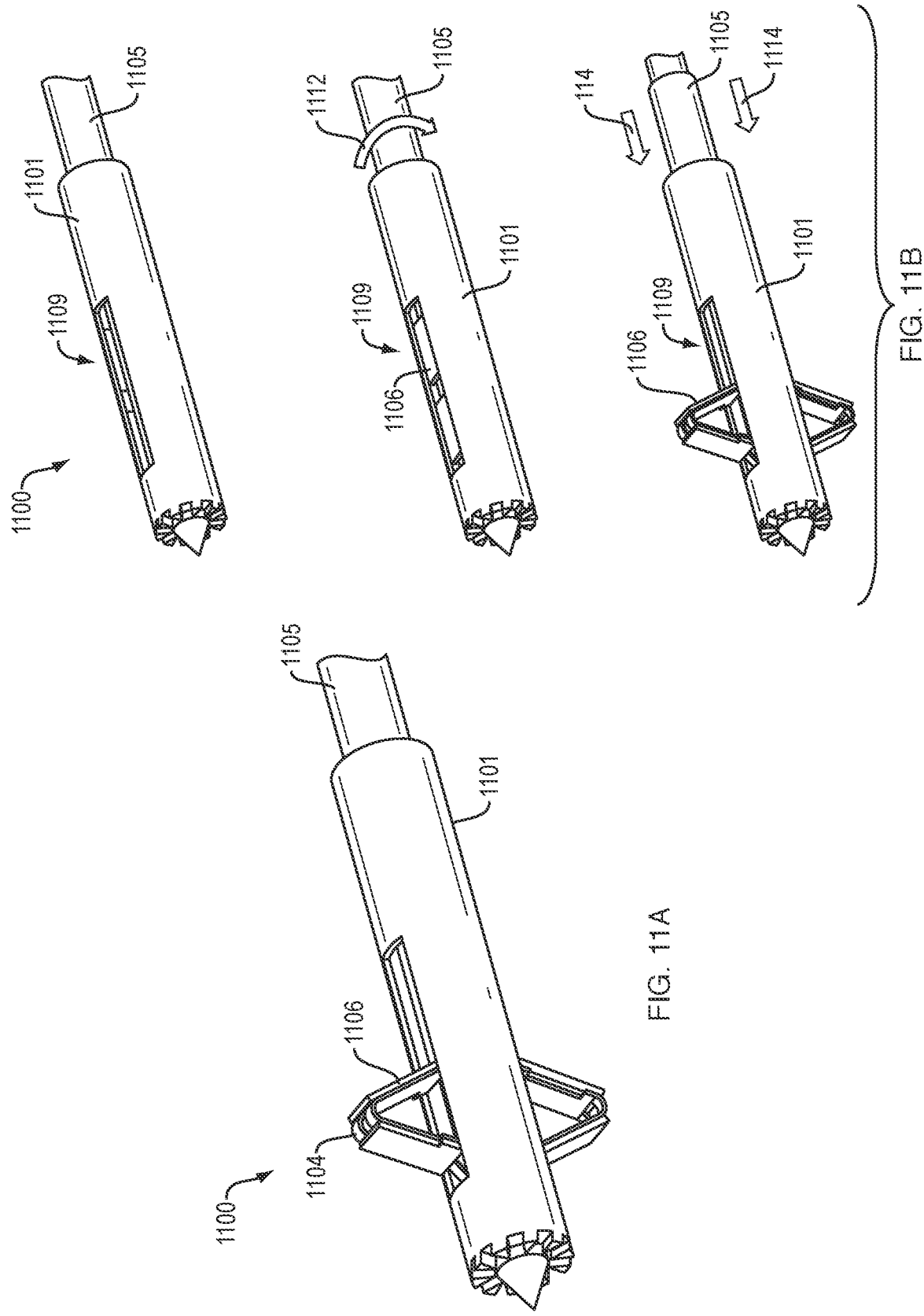

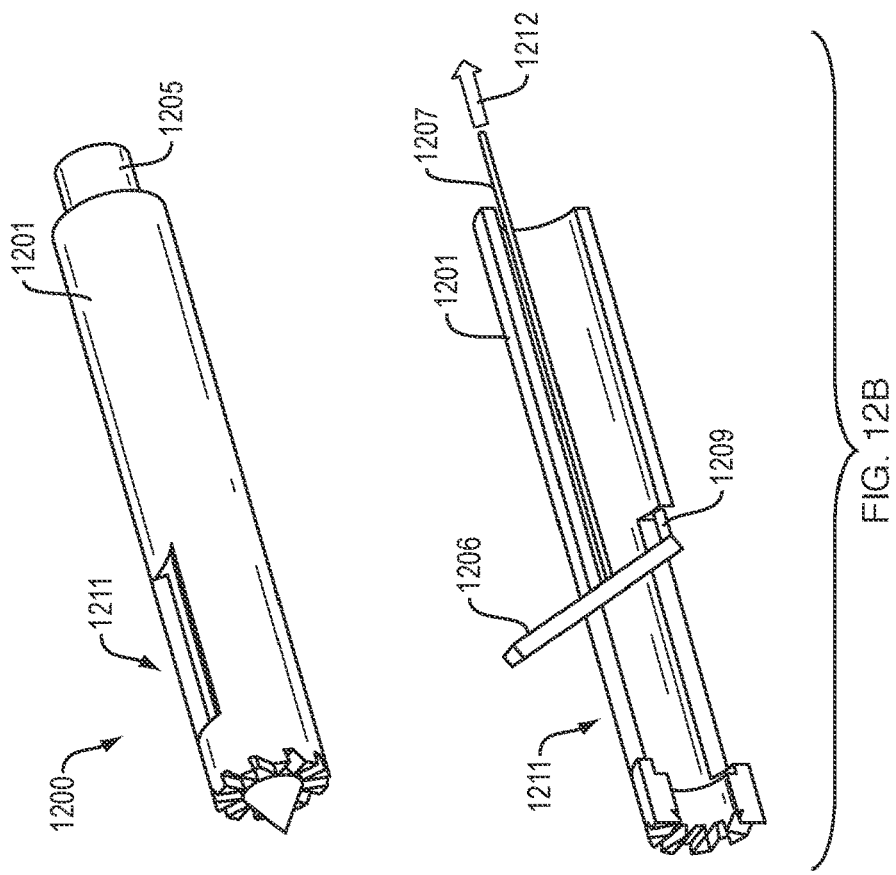
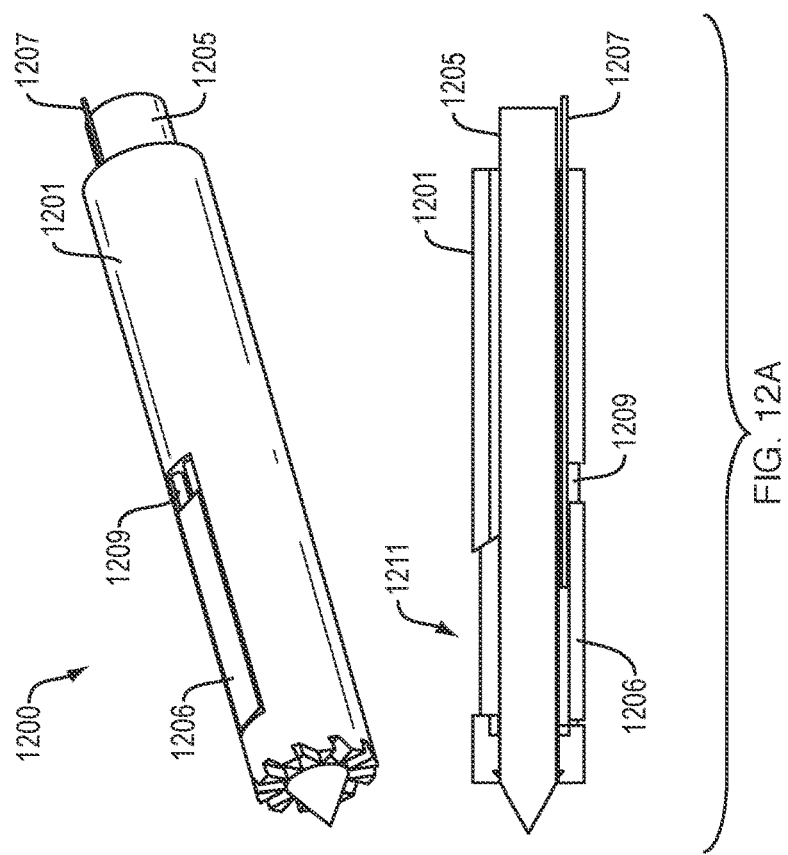
FIG. 12A
FIG. 12B

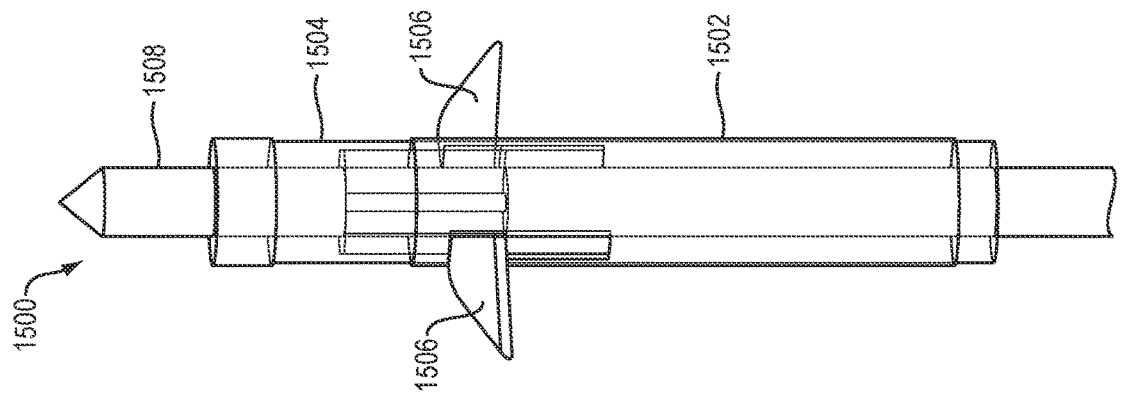
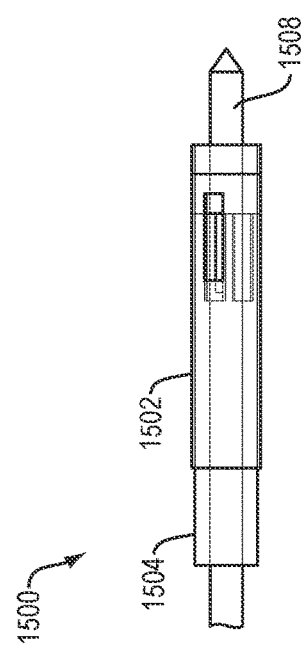
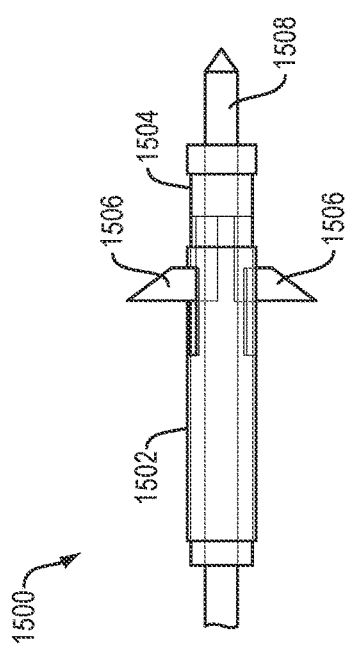

SURGICAL INSTRUMENT

CROSS REFERENCE TO RELATED APPLICATIONS

This application is a continuation of co-pending U.S. patent application Ser. No. 16/409,987 filed May 13, 2019 entitled SURGICAL INSTRUMENT, which in turn is a divisional of U.S. patent application Ser. No. 14/096,660 filed Dec. 4, 2013 entitled SURGICAL INSTRUMENT, now U.S. Pat. No. 10,357,259, which in turn claims benefit of the priority of U.S. Provisional Patent Application No. 61/733,479 filed Dec. 5, 2012 entitled SURGICAL INSTRUMENT, and U.S. Provisional Patent Application No. 61/757,843 filed Jan. 29, 2013 entitled SURGICAL INSTRUMENT, the entire contents of which are incorporated herein by reference for all purposes.

TECHNICAL FIELD

The present application relates generally to surgical instruments, and more specifically to surgical instruments having at least one cutting member, such as a rotatable blade for use in retrograde cutting of bone.

BACKGROUND

Some surgeons have performed anterior cruciate ligament (ACL) surgery using a retrograde approach to create the femoral ACL tunnels (i.e., "All-Inside ACL Reconstruction"). As illustrated in FIG. 1, this approach typically requires a surgical instrument 100 that can drill a tunnel 102 in a retrograde fashion, as the surgeon pulls-back (see directional arrow 108) on the retrograde reamer 104 from a bone joint space 106 towards the lateral femoral cortex. However, such a surgical instrument tends to create a tunnel that is not truly circular, or worse, the tunnel can be created along a pathway that diverges from the intended trajectory, and thus may not be anatomic and/or may cause injury to neurovascular structures, etc. In addition, such a surgical instrument is generally specific for creating tunnels of a certain fixed diameter, which requires having access to a large inventory of instruments for one surgical case.

Moreover, surgeons who conduct ACL reconstruction generally prefer to mimic the natural anatomy to achieve optimal results. The placement of a tendon graft in the original footprint of the ACL is generally referred to as "anatomic ACL reconstruction". One feature of anatomic ACL reconstruction is the proper placement of the tunnels for the tendon graft. The tunnel exit in the space of the bone joint should be accurate to ensure the functionality of the graft. Further, the tunnel exit on the lateral side of the femur (thigh) should be appropriately placed to ensure adequate tunnel length. It would be desirable to have improved surgical instruments that can assist the surgeon in the proper placement of the femoral tunnel.

SUMMARY

In accordance with the present application, a retrograde reamer is disclosed that is adjustable to create tunnels of multiple different diameters. In one aspect, the disclosed retrograde reamer is cannulated. In another aspect, the disclosed retrograde reamer is configured to create tunnels having distinct stepped diameters. In still another aspect, the disclosed retrograde reamer includes at least one cutting member, and a mechanism operative to gradually move the cutting member from a deployed position to a stored, closed, or collapsed position to create a tapered tunnel. The mechanism can be linked to rotations of the cutting member so that, for predetermined numbers of rotations, the cutting member moves specified distances toward the stored, closed, or collapsed position.

In a further aspect, the disclosed retrograde reamer includes a first tubular shaft having a sidewall, which includes at least one opening therethrough. The retrograde reamer further includes a second shaft movably disposed within the first tubular shaft, and at least one cutting member movably disposed in the first tubular shaft. The cutting member is operative, in response to the second shaft moving from a first position to a second position within the first tubular shaft, to move through the opening to an outside position that is at least partially outside the first tubular shaft, thereby defining a cutting diameter.

The disclosed cannulated retrograde reamer can be configured to accommodate a guide wire. Further, the cannulated retrograde reamer substantially reduces the risk of tunnel malposition and/or misalignment, and can be adjusted to create a range of tunnel diameters, thereby allowing inventory levels to be reduced for a surgical case.

Other features, functions, and aspects of the invention will be evident from the Detailed Description that follows.

BRIEF DESCRIPTION OF THE DRAWINGS

The accompanying drawings, which are incorporated in and constitute a part of this specification, illustrate one or more embodiments described herein and, together with the Detailed Description, explain these embodiments. In the drawings:

FIGS. 9a and 9b illustrate a third alternative embodiment of the retrograde reamer of FIG. 2;

FIGS. 10a and 10b illustrate a fourth alternative embodiment of the retrograde reamer of FIG. 2;

FIGS. 11a and 11b illustrate a fifth alternative embodiment of the retrograde reamer of FIG. 2;

FIGS. 12a and 12b illustrate a sixth alternative embodiment of the retrograde reamer of FIG. 2;

FIGS. 15*a*-15*c* illustrate a ninth alternative embodiment of the retrograde reamer of FIG. 2.

DETAILED DESCRIPTION

The disclosures of U.S. Provisional Patent Application No. 61/733,479 filed Dec. 5, 2012 entitled SURGICAL INSTRUMENT, and U.S. Provisional Patent Application No. 61/757,843 filed Jan. 29, 2013 entitled SURGICAL INSTRUMENT, are hereby incorporated herein by reference in their entirety.

Figure 1:
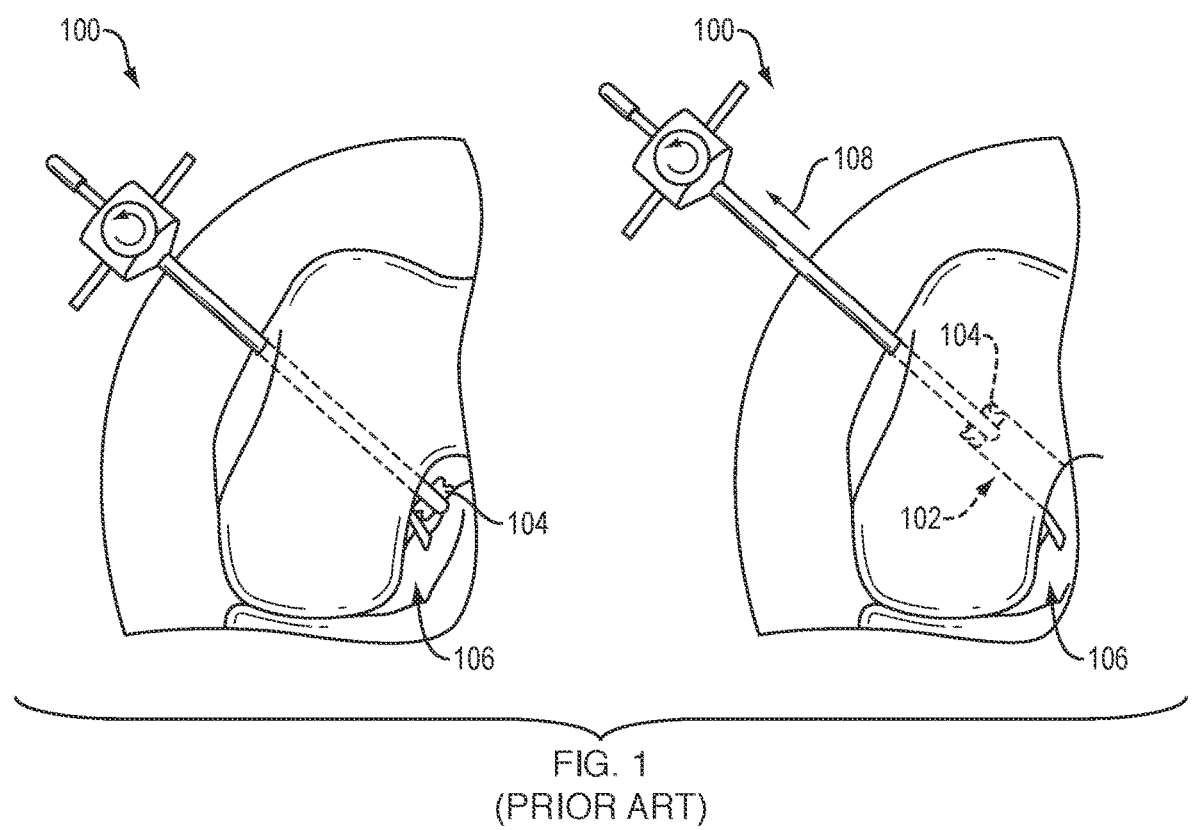
FIG. 1 is a diagram of a conventional surgical instrument configured to drill tunnels through bone in a retrograde fashion.
Figure 2:
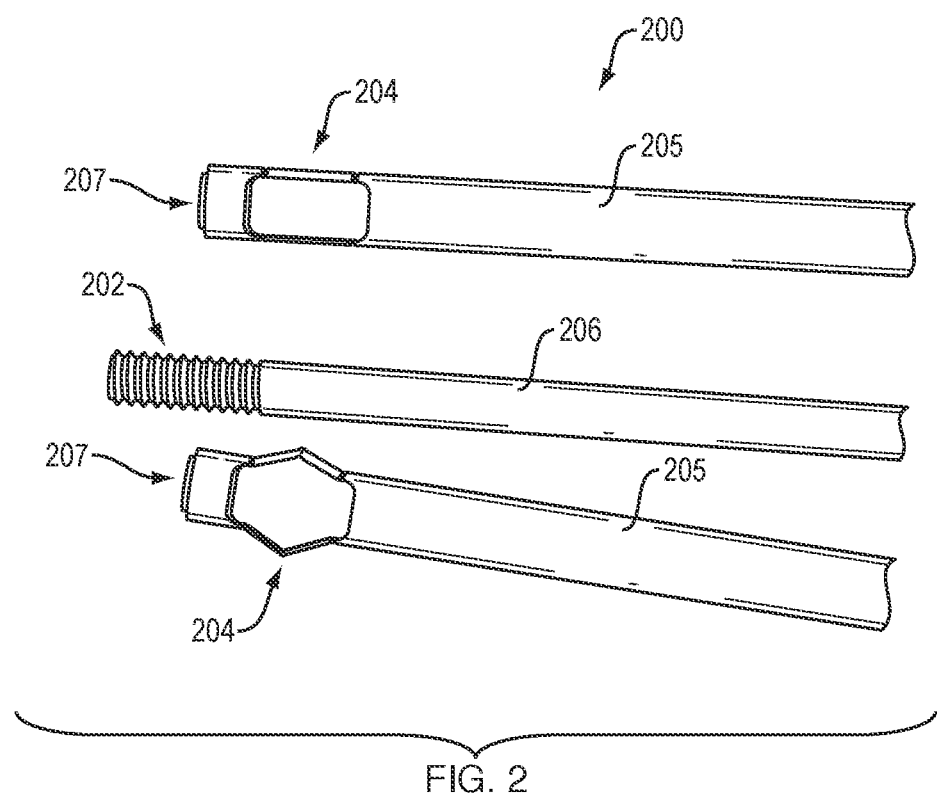
FIG. 2 is an illustration of an exemplary surgical instrument (also referred to herein as the "retrograde reamer") configured to drill tunnels through bone in a retrograde fashion, in accordance with the present application.

With reference to FIG. 2, an illustrative embodiment of components of an exemplary surgical instrument 200 (also referred to herein as the "retrograde reamer") is disclosed, in accordance with the present application. As shown in FIG. 2, the components of the retrograde reamer 200 include an elongated inner shaft 206, an elongated outer tubular shaft 205, and a plurality of cutting members 204 movably coupled to the elongated outer tubular shaft 205. The outer tubular shaft 205 includes internal threads at a distal end 207 thereof. The plurality of cutting members 204 (e.g., two (2) cutting members) are located near the distal end 207 of the outer tubular shaft 205. The inner shaft 206 includes an externally threaded distal tip 202.

When the retrograde reamer 200 is assembled, the inner shaft 206 is rotationally mounted within the elongated outer tubular shaft 205 such that the threaded distal tip 202 is engaged with the internal threads at the distal end 207 of the outer tubular shaft 205. To deploy and actuate the cutting members 204, the inner shaft 206 is rotated repeatedly (i.e., multiple revolutions), thereby causing the distal end 207 of the outer tubular shaft 205 to move toward a proximal end of the outer tubular shaft 205. As the inner shaft 206 turns and the distal end 207 of the outer tubular shaft 205 moves proximally, the two (2) cutting members 204 near the distal end 207 of the outer tubular shaft 205 flex and expand outwardly, creating a progressively increasing cutting diameter. Once the cutting members 204 have reached a desired position, the relative positions of the inner shaft 206 and the outer tubular shaft 205 can be locked. The retrograde reamer 200 can then be rotated (such as by a drill) to create a retrograde tunnel having a desired diameter.

To remove the retrograde reamer 200 from a bone joint after tunnel creation, the inner shaft 206 is rotated in the opposite direction, thereby causing the distal end 207 of the outer tubular shaft 205 to move distally, and the cutting members 204 to flex back, and close or collapse to their pre-deployment (i.e., flat) configuration. Once the cutting members 204 have returned to their pre-deployment configuration, the retrograde reamer 200 can be removed from the surgical site.

It is noted that two or more cutting members like the cutting members 204 may be provided. For example, three, four, five, six, or any other suitable number of cutting members may be incorporated in the retrograde reamer 200. Further, the cutting members 204 may be hinged, and/or may have sharpened edges. The sharpened edges may be coated with a metal or metal alloy, or diamond-like carbon to enhance strength and cutting performance.

It is further noted that the inner shaft 206 can be cannulated to accommodate a guide wire. The retrograde reamer 200 may also be connected to suction means so that cut tissue can be aspirated from the surgical site through the cannulated inner shaft 206. The inner shaft 206 could also include a handle with a counter that could indicate the current tunnel diameter as a function of the number of shaft revolutions. The mechanical force generated during retraction/closure of the cutting members 204 after tunnel creation can be made to overcome the resistance of any residual tissue caught in the cutting members 204. The presence of such residual tissue is a frequent nuisance of conventional retrograde reamers.

In addition, the inner shaft 206 can be replaced with a shaft that is connected to the distal end 207 of the outer tubular shaft 205 to enable control of cutter deployment by a ratchet-locking system, or any other suitable locking mechanism. The locking mechanism can be located at a proximal end of the retrograde reamer 200. The ratchet-locking system can be configured to adjust the cutting diameter of the cutting members 204 by ratcheting in either direction. The axial position of the inner shaft 206 can be locked (e.g., by teeth) at the desired cutting diameter. When engaged, such teeth can prevent the inner shaft 206 from moving. When disengaged, the inner shaft 206 is movable. Movement of the inner shaft 206 in a proximal direction activates the cutting members 204 and increases the cutting diameter. Movement of the inner shaft 206 in a distal direction decreases the cutting diameter and effectively deactivates the cutting members 204. In some embodiments, the locking mechanism may be configured to be similar to a cable tie.

Figure 3A:
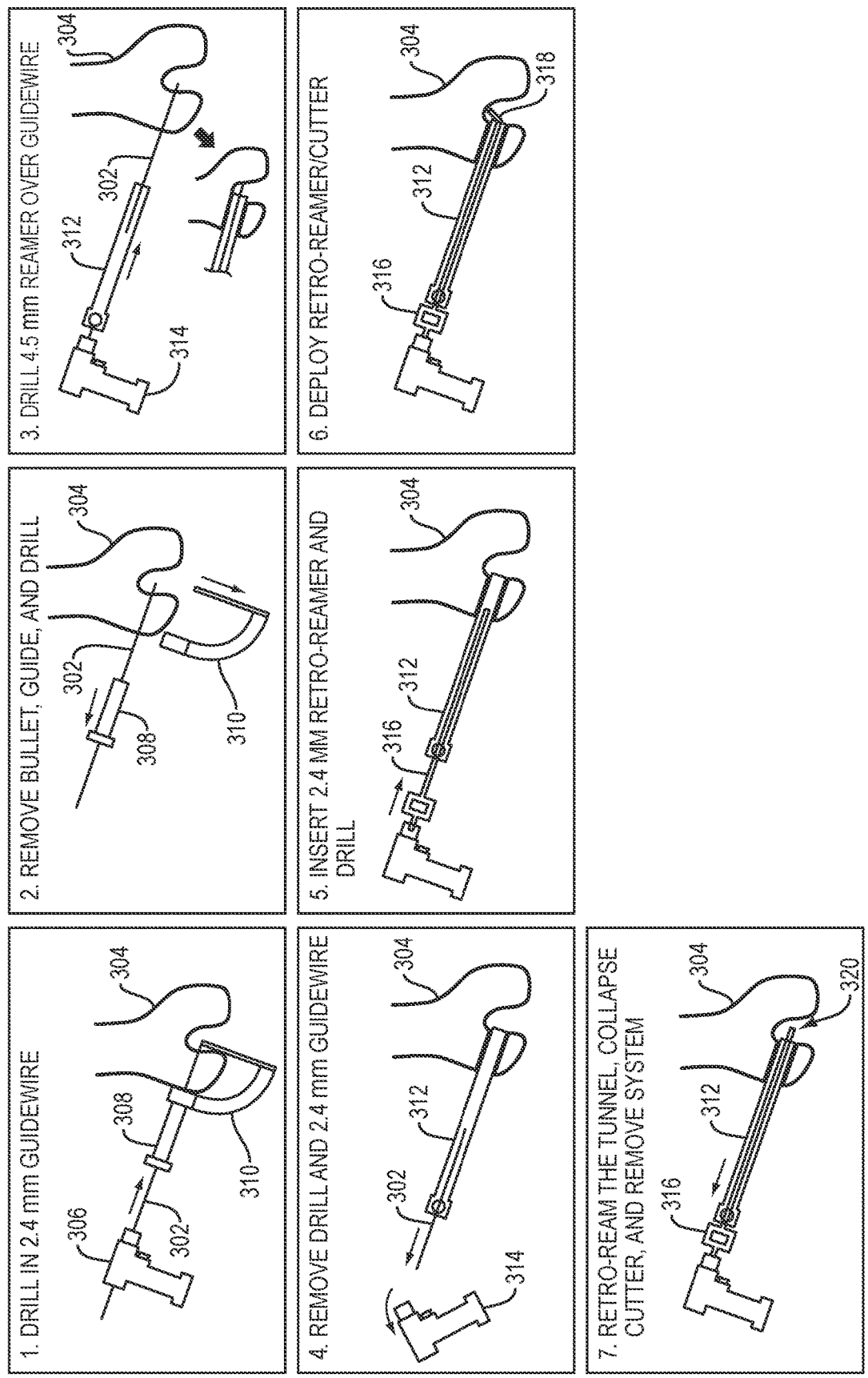
FIGS. 3a-3c depict diagrams of a first illustrative example of use of the retrograde reamer of FIG. 2.
Figure 3B:
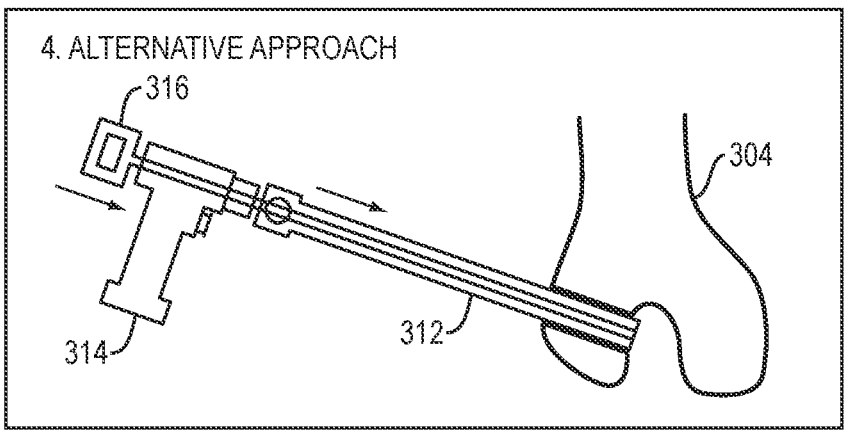

The disclosed surgical instrument will be further understood with reference to the following illustrative examples. In a first illustrative example, as described with reference to steps 1-7 of FIG. 3*a*, a retrograde reamer, such as a 2.4 mm retrograde reamer 316, is employed in conjunction with a 4.5 mm reamer. As depicted in step 1 (see FIG. 3*a*), a 2.4 mm guide wire 302 is drilled into a bone joint 304 using a suitable drill 306, bullet 308, and guide 310. As depicted in step 2, the bullet 308, the guide 310, and the drill 306 are removed. As depicted in step 3, a 4.5 mm reamer 312 is drilled over the guide wire 302 using a suitable drill 314. As depicted in step 4, the drill 314 and the 2.4 mm guide wire 302 are removed. As depicted in step 5, the 2.4 mm retrograde reamer 316 is inserted into the 4.5 mm reamer 312. For example, the 2.4 mm retrograde reamer 316 can extend out of a distal end of the 4.5 mm reamer 312, or extend through windows in the 4.5 mm reamer 312. As depicted in step 6, a cutting member 318 of the 2.4 mm retrograde reamer 316 is deployed. As depicted in step 7, after the 2.4 mm retrograde reamer 316 is used to retro-ream a tunnel 320 through the bone joint 304, the cutting member 318 is closed or collapsed, and the surgical instrument system is removed. FIG. 3*b* depicts an alternative to step 4 of FIG. 3*a*, in which only the 2.4 mm guide wire 302 is removed, and the 2.4 mm retrograde reamer 316 is inserted through the back end of the drill 314.

Figure 3C:
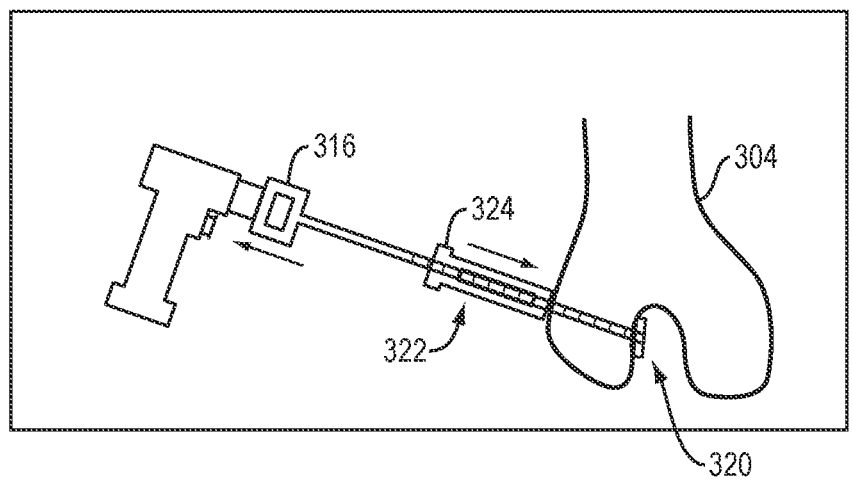

With further regard to the first illustrative example, FIG. 3*c* depicts how the tunnel 320 can be measured using a measurement gauge 322 inside the bone joint 304. As shown in FIG. 3*c*, the measurement gauge 322 can be held against the bone joint 304 during the retro-reaming operation. Further tunnel measurement options include (1) using the measurement gauge 322 on the outside of the bone joint 304 to visualize the reamer markings, (2) leaving only the bullet 308 in place while measuring the tunnel 320, (3) leaving both the bullet 308 and the guide 310 in place while measuring the tunnel 320, and (4) using, on the outside of the 4.5 mm reamer 312, a measurement sleeve 324 (see FIG. 3*c*) that is manually held against the bone joint 304.

Figure 4:
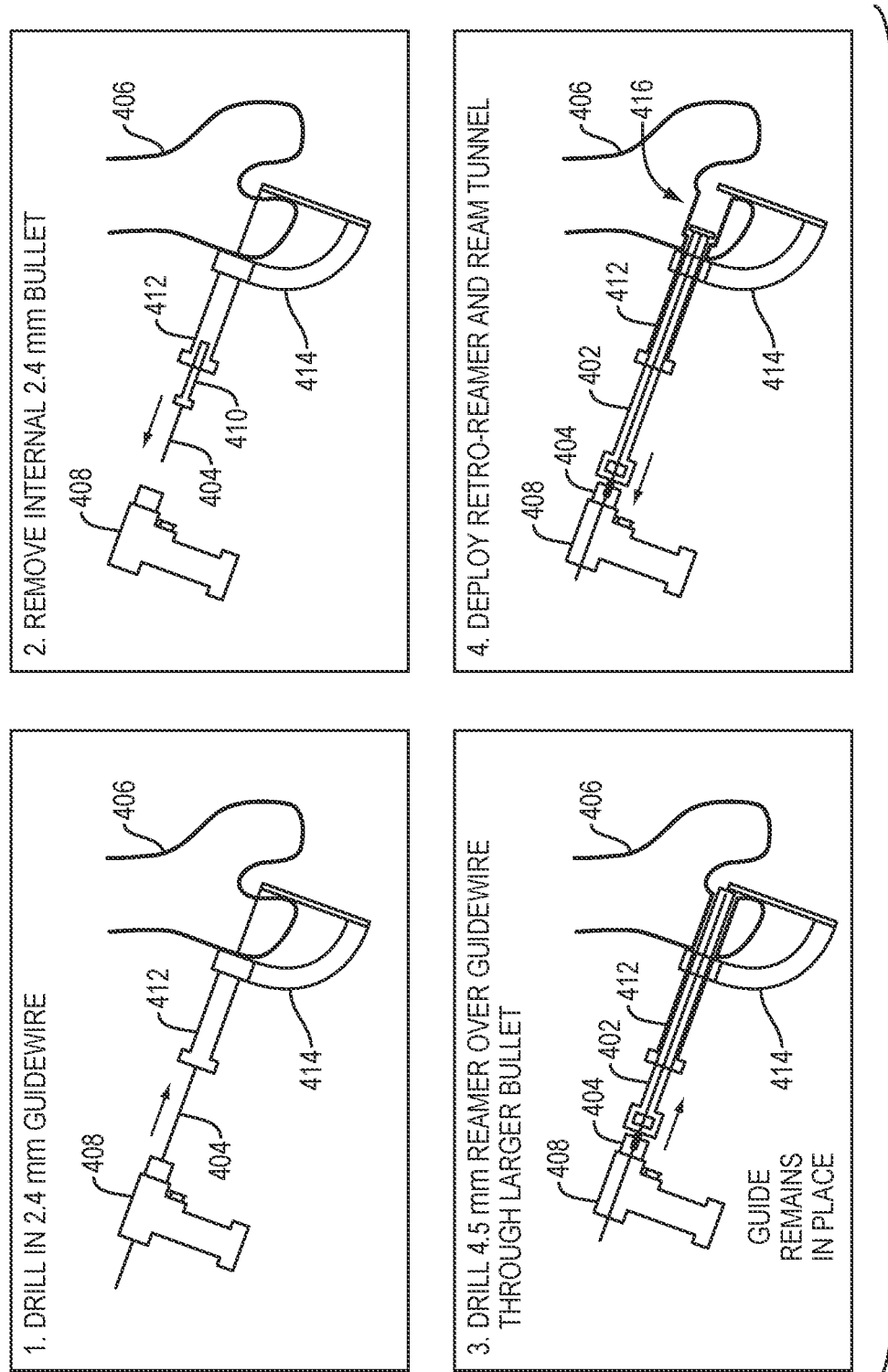
FIG. 4 depicts diagrams of a second illustrative example of use of the retrograde reamer of FIG. 2.

In a second illustrative example, as described with reference to steps 1-4 of FIG. 4, a 4.5 mm reamer 402 is employed as a retro-reaming instrument. As depicted in step 1 (see FIG. 4), a 2.4 mm guide wire 404 is drilled into a bone joint 406 using a suitable drill 408, bullets 410, 412, and guide 414. As depicted in step 2, the internal 2.4 mm bullet 410 is removed. As depicted in step 3, the 4.5 mm reamer 402 is operated, using the drill 408, to drill a tunnel, from the outside in, over the guide wire 404 through the larger bullet 412 with the guide 414 in place. As depicted in step 4, the 4.5 mm retro-reaming instrument 402 is used to retro-ream a tunnel 416 through the bone joint 406. With reference to this second illustrative example, the 4.5 mm retro-reaming instrument 402 can be self-actuating. Alternatively, a 2.4 mm actuator rod can be employed to actuate the 4.5 mm retro-reaming instrument 402 to retro-ream the tunnel 416 through the bone joint 406.

Figure 5:
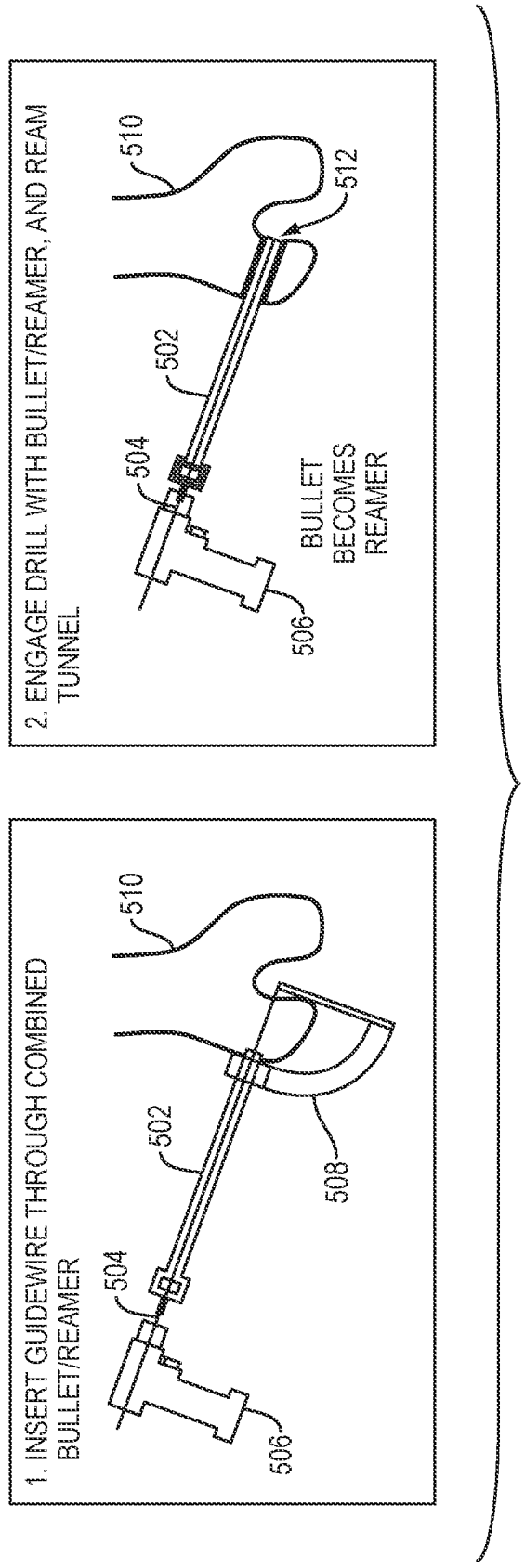
FIG. 5 depicts diagrams of a third illustrative example of use of the retrograde reamer of FIG. 2.

In a third illustrative example, as described with reference to steps 1-2 of FIG. 5, a 4.5 mm reamer 502 is employed as the bullet for a guide wire 504. As depicted in step 1 (see FIG. 5), using a suitable drill 506 and guide 508, the guide wire 504 is inserted in a bone joint 510 through the combined bullet/4.5 mm reamer 502. As depicted in step 2, the drill 506 is engaged with the combined bullet/4.5 mm reamer 502, and a 4.5 mm tunnel 512 is reamed through the bone joint 510. In effect, the bullet becomes the 4.5 mm reamer 502. Allowing the 4.5 mm reamer 502 to serve as the bullet reduces the need to remove the bullet after drilling the guide wire 504. It is noted that a holder for the bullet may be configured to allow lateral removal of the guide 508.

Figure 6:
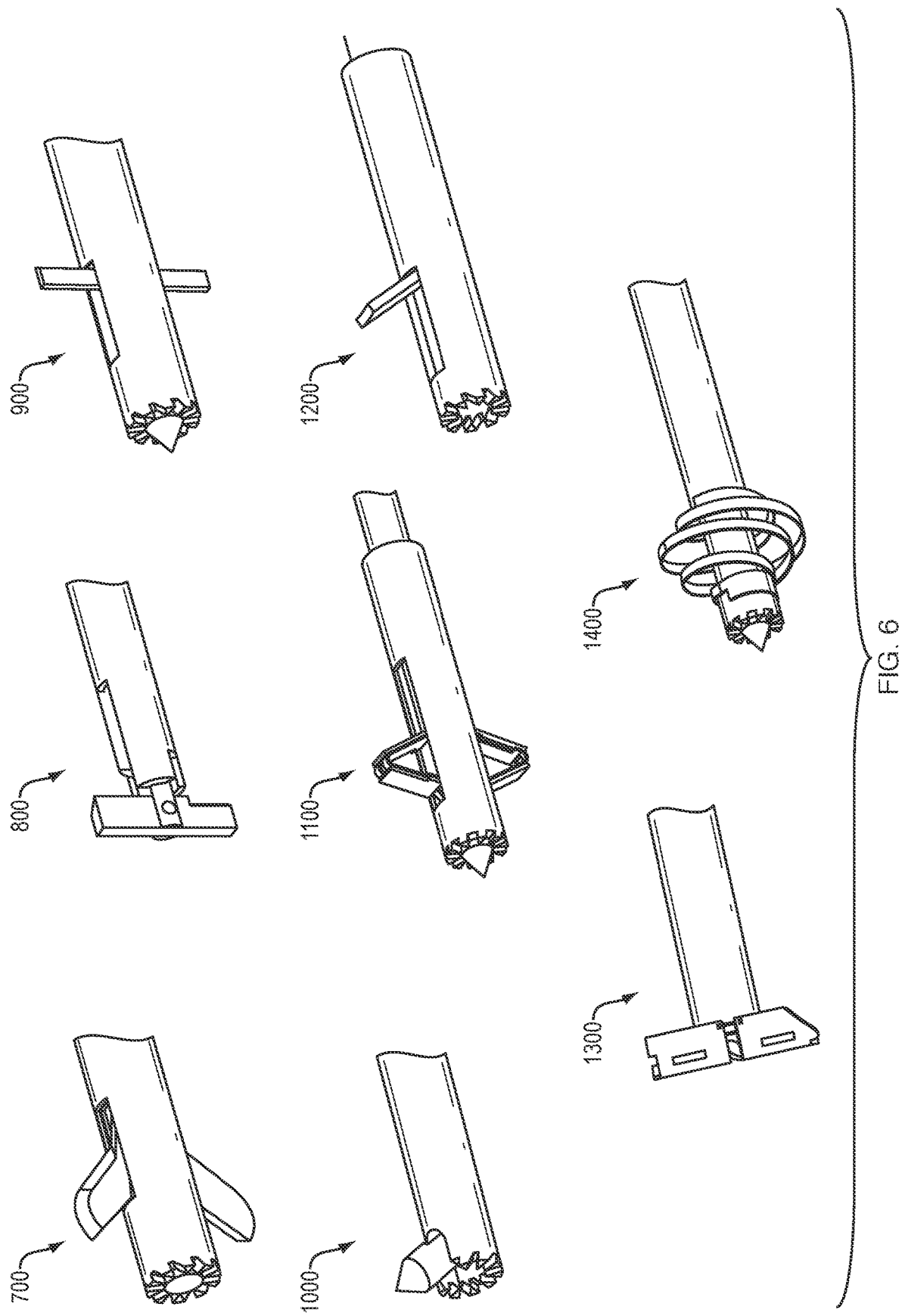
FIG. 6 illustrates a plurality of alternative embodiments of the retrograde reamer of FIG. 2.
Figure 7A:
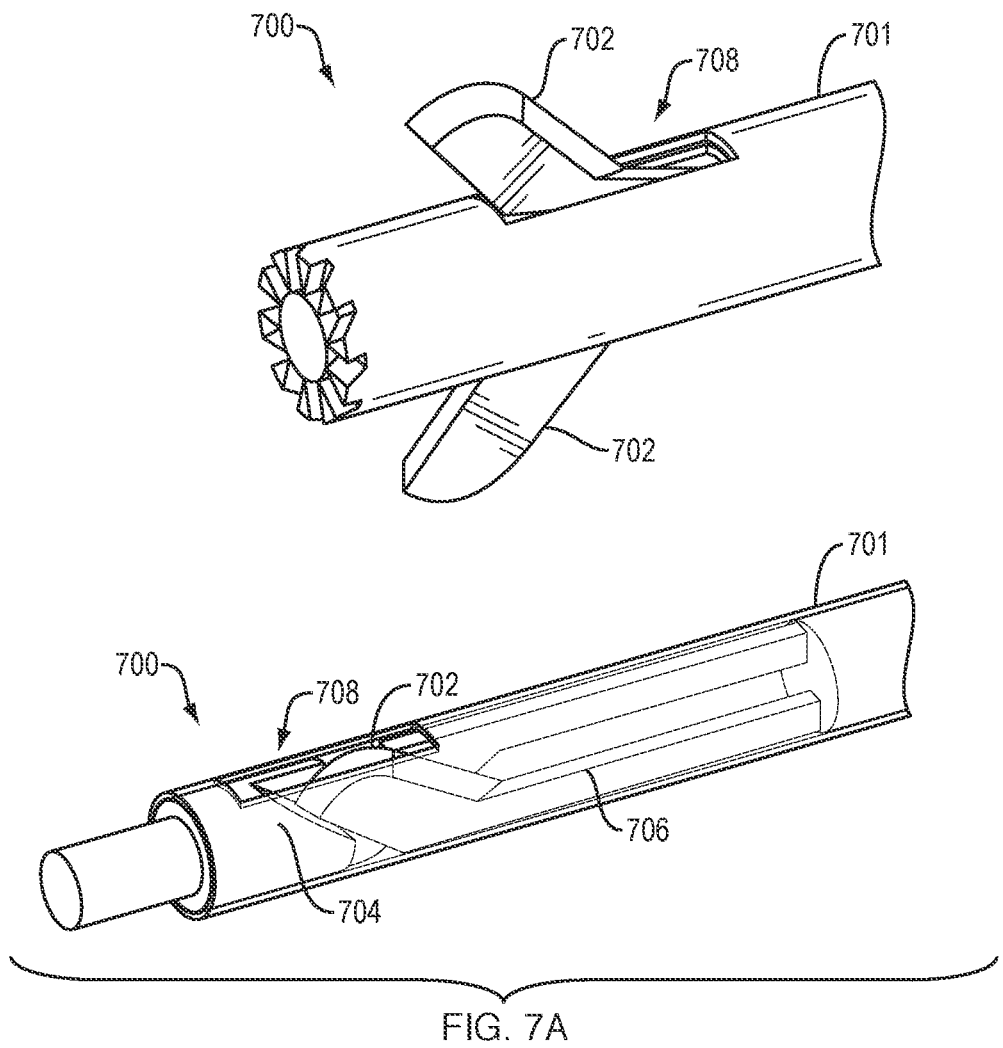
FIGS. 7a and 7b illustrate a first alternative embodiment of the retrograde reamer of FIG. 2.
Figure 7B:
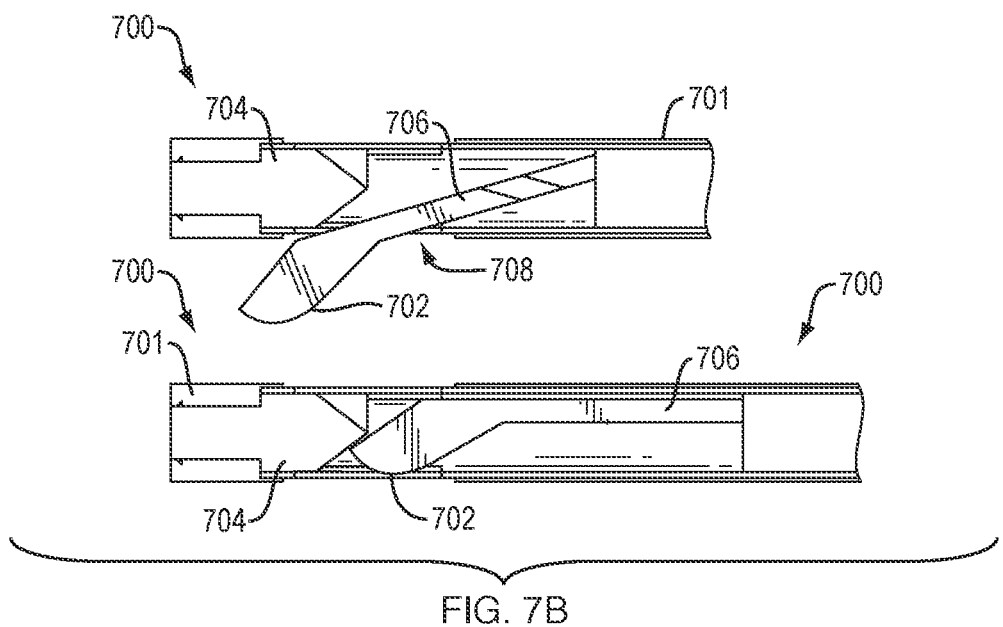

FIG. 6 depicts a plurality of alternative embodiments 700, 800, 900, 1000, 1100, 1200, 1300, 1400 of the disclosed retrograde reamer. As shown in FIGS. 7a and 7b, the retrograde reamer 700 includes one or more blades 702, one or more wedge members 704, and one or more flex members 706. During use, the guide wire is typically removed from the surgical site, and the blades 702 connected to the respective flex members 706 are inserted into a tubular shaft 701 of, for example, a 4.5 mm reamer, thereby causing the blades 702 to impinge against the respective wedge members 704 and move in a radial fashion out of the shaft 701 through corresponding slots 708 in the shaft 701. In some embodiments, the shaft 701 can have a stepped internal diameter. Further, in some embodiments, the flex members 706 can be implemented as hinges. The blades 702 connected to the respective flex members 706 can be advanced through the tubular shaft 701 to deploy the blades 702, and subsequently retracted into the shaft 701 to close or collapse the blades 702. The diameters of tunnels created using the retrograde reamer 700 are adjustable based on how far the wedge members 704 drive the blades 702 through the respective slots 708 in the shaft 701. Alternatively, the diameters of tunnels created using the alternative configuration 700 can be fixed. It is noted that the retrograde reamer 700 can be keyed to fenestrations of the 4.5 mm reamer.

Figure 8B:
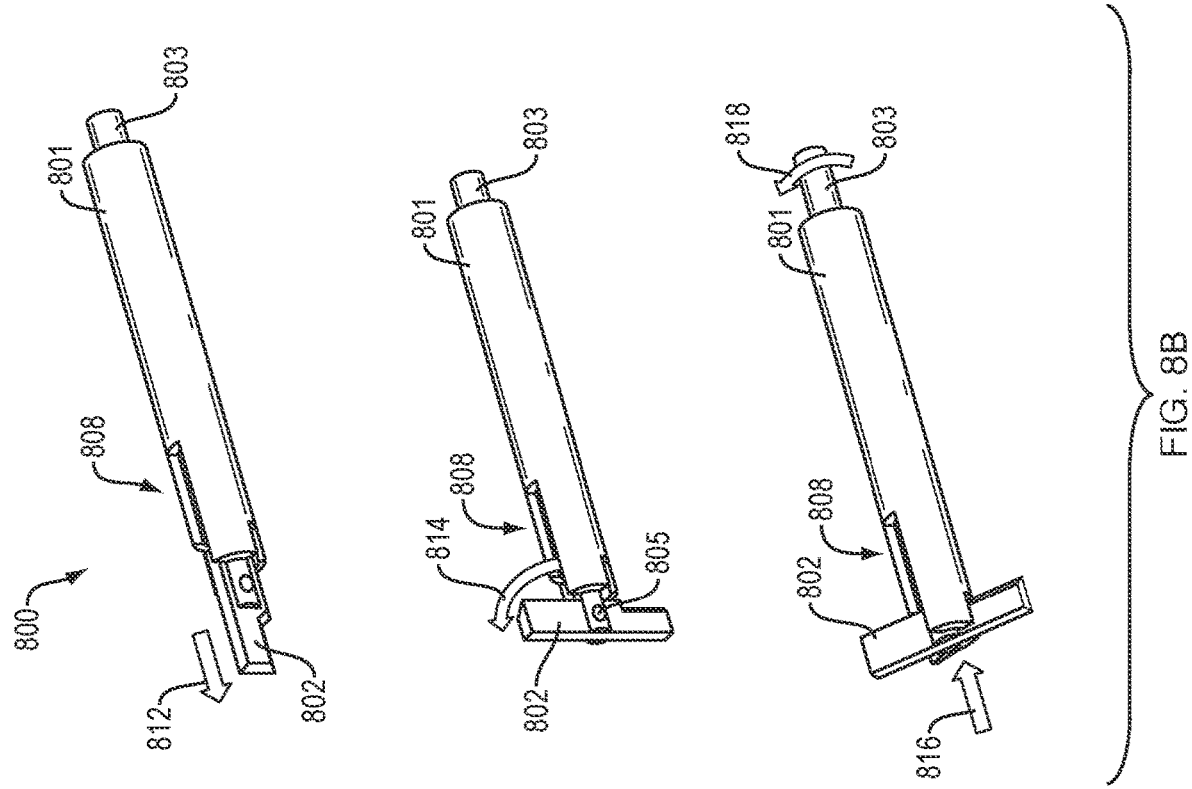
FIGS. 8a and 8b illustrate a second alternative embodiment of the retrograde reamer of FIG. 2.
Figure 8A:
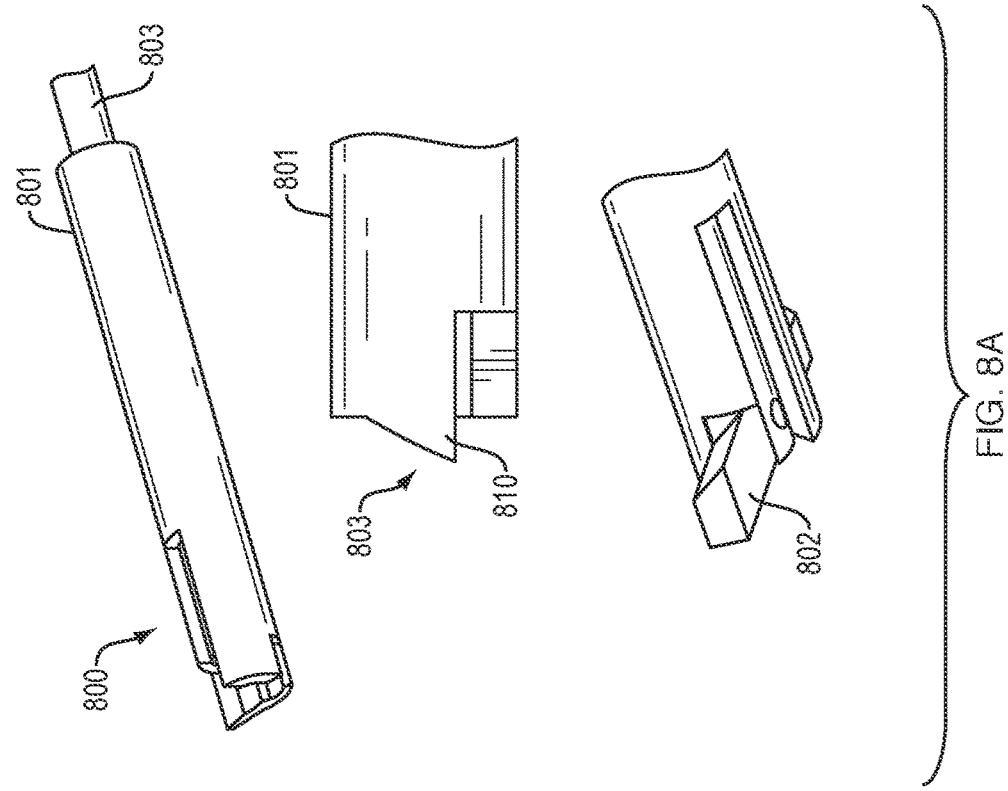

FIGS. 8a and 8b depict detailed views of the alternative configuration 800 of the retrograde reamer. As shown in FIGS. 8a and 8b, the retrograde reamer 800 includes a shaft 803, and one or more blades 802 connected by a pivot 805 to a distal end of the shaft 803. In some embodiments, the shaft 803 can have a reamer tooth 810 at its distal end. During use, the guide wire is typically removed from the surgical site, and the shaft 803 and blades 802 are inserted into a tubular shaft 801 of, for example, a 4.5 mm reamer. In this case, the blades 802 can be keyed to support slots 808 in the shaft 801. To deploy the blades 802, the pivot 805 is advanced past a distal end of the shaft 801 (see directional arrow 812), a toggling mechanism pivotably places the blades 802 in a cutting position (see directional arrow 814), and the shaft 803 is rotated, for example, by a quarter turn (see directional arrow 818), and then retracted into the shaft 801 to place the blades 802 into the corresponding support slots 808 (see directional arrow 816). To close or collapse the blades 802, the pivot 805 is advanced past the distal end of the tubular shaft 801 (see directional arrow 812) to pivotally place the blades 802 along the longitudinal axis of the shaft 803, and the shaft 803 is rotated by a quarter turn (see directional arrow 818) and then retracted back into the shaft 801 (see directional arrow 816). In some embodiments, the retrograde reamer 800 can include a single-sided blade (L-shaped blade configuration), or double-sided blades (T-shaped blade configuration). The diameters of tunnels created using the L-shaped or T-shaped blade configuration are typically fixed. It is noted that the L-shaped blade configuration generally requires less penetration into a bone joint space for deployment. It is further noted that the toggle mechanism for deploying the blades 802 can be implemented using torsion springs, pull wires, a push rod, a spring plunger, or any other suitable toggle mechanism.

FIGS. 9a and 9b depict detailed views of the alternative configuration 900 of the retrograde reamer. As shown in FIGS. 9a and 9b, the retrograde reamer 900 includes an internal shaft 903, a tubular external shaft 905, and one or more blades 902. In some embodiments, the distal end of the external shaft 905 can have a pointed or sharpened tip. During use, the external shaft 905 can function as a guide wire. To deploy the blades 902, the internal shaft 903 is retracted into the tubular shaft 905 (see directional arrow 912), causing the blades 902 to deploy through corresponding slots 909 in the shafts 903, 905, as well as through corresponding slots 908 in a tubular shaft 901 of, for example, a 4.5 mm reamer. To collapse the blades 902, the internal shaft 903 is advanced into the tubular shaft 905. In some embodiments, the retrograde reamer 900 includes a single blade. The diameters of tunnels created using the blades 902 are typically fixed. It is noted that the mechanism for deploying the blades 902 can be implemented using torsion springs, pull wires, a push rod, a spring plunger, or any other suitable mechanism. It is further noted that the retrograde reamer 900 can be keyed to fenestrations of the 4.5 mm reamer.

FIGS. 10a and 10b depict detailed views of the alternative configuration 1000 of the retrograde reamer. As shown in FIGS. 10a and 10b, the retrograde reamer 1000 includes a shaft 1005 having a pivotable distal end 1007 with a pointed or sharpened tip. During use, the guide wire is typically removed from the surgical site, and the shaft 1005 is inserted into a tubular shaft 1001 of, for example, a 4.5 mm reamer. To deploy the pointed or sharpened tip of the pivotable distal end 1007, the distal end 1007 of the shaft 1005 is advanced past a distal end of the 4.5 mm reamer (see directional arrow 1012), the distal end 1007 is rotated up to 180° at a pivotable joint to a cutting position (see directional arrow 1014), and the shaft 1005 is retracted to place the distal end 1007 into a support slot 1009 in the shaft 1001 (see directional arrow 1016). To close or collapse the pointed or sharpened tip of the pivotable distal end 1007, the shaft 1005 is advanced past the distal end of the 4.5 mm reamer (see directional arrow 1012), the distal end 1007 is rotated to pivotally place the distal end 1007 along the longitudinal axis of the shaft 1005, and the shaft 1005 is retracted back into the tubular shaft 1001 (see directional arrow 1016). The diameters of tunnels created using the pivotable distal end 1007 are typically fixed. It is noted that the mechanism for deploying the pivotable distal end 1007 can be implemented using a torsion coil 1004, a laser cut hypotube, a micro-universal joint, or any other suitable mechanism. In some embodiments, the shaft 1005 can function as the guide wire. In addition, in some embodiments, the pivotable joint of the pivotable distal end 1007 can have more than one seating position.

FIGS. 11*a* and 11*b* depict detailed views of the alternative configuration 1100 of the retrograde reamer. As shown in FIGS. 11*a* and 11*b*, the retrograde reamer 1100 includes a shaft 1105 having a distal end with a pointed or sharpened tip, and one or more blades 1106 attached to one or more flex members 1104. For example, the flex members 1104 can be made from a Nitinol alloy, or any other suitable material. During use, the shaft 1105 and blades 1106 are inserted into a tubular shaft 1101 of, for example, a 4.5 mm reamer. To deploy the blades 1106, the shaft 1105 is rotated to position the blades 1106 in registration with slots 1109 in the shaft 1101 (see directional arrow 1112), and then advanced to move the blades 1106 attached by the flex member 1104 through the slots 1109 (see directional arrows 1114). To close or collapse the blades 1106, the shaft 1105 is retracted, closing or collapsing the blades 1106 within the shaft 1101, and then rotated to move the blades 1106 away from the slots 1109. In some embodiments, the Nitinol alloy can be employed as the cutting member. The diameters of tunnels created using the alternative configuration 1100 are adjustable based on how far the blades 1106 are deployed through the slots 1109. Alternatively, the diameters of tunnels created using the alternative configuration 1100 can be fixed.

FIGS. 12*a* and 12*b* depict detailed views of the alternative configuration 1200 of the retrograde reamer. As shown in FIGS. 12*a* and 12*b*, the retrograde reamer 1200 includes a shaft 1205 having a distal end with a pointed or sharpened tip, and one or more blades 1206 attached to a sidewall of a tubular shaft 1201 (e.g., a 4.5 mm reamer) by one or more flex members 1209. During use, the shaft 1205 is inserted into the tubular shaft 1201 of the 4.5 mm reamer. To deploy the blades 1206, the shaft 1205 is retracted through the tubular shaft 1201, and a deployment member such as a wire 1207 (e.g., a flat wire or rod) connected to the blade 1206 is pulled to deploy the blade 1206 through a slot 1211 in the shaft 1201 (see directional arrow 1212). To close or collapse the blades 1206, the shaft 1205 is advanced into the tubular shaft 1201, impinging against the blade 1206 and closing or collapsing the blade 1206 within the shaft 1201. The diameters of tunnels created using the retrograde reamer 1200 can be adjustable based on how far the wire 1207 deploys the blade 1206 through the slot 1211 in the shaft 1201. Alternatively, the diameters of tunnels created using the retrograde reamer 1200 can be fixed. It is noted that the retrograde reamer 1200 of the retrograde reamer can be keyed to fenestrations of the 4.5 mm reamer.

Figure 13B:
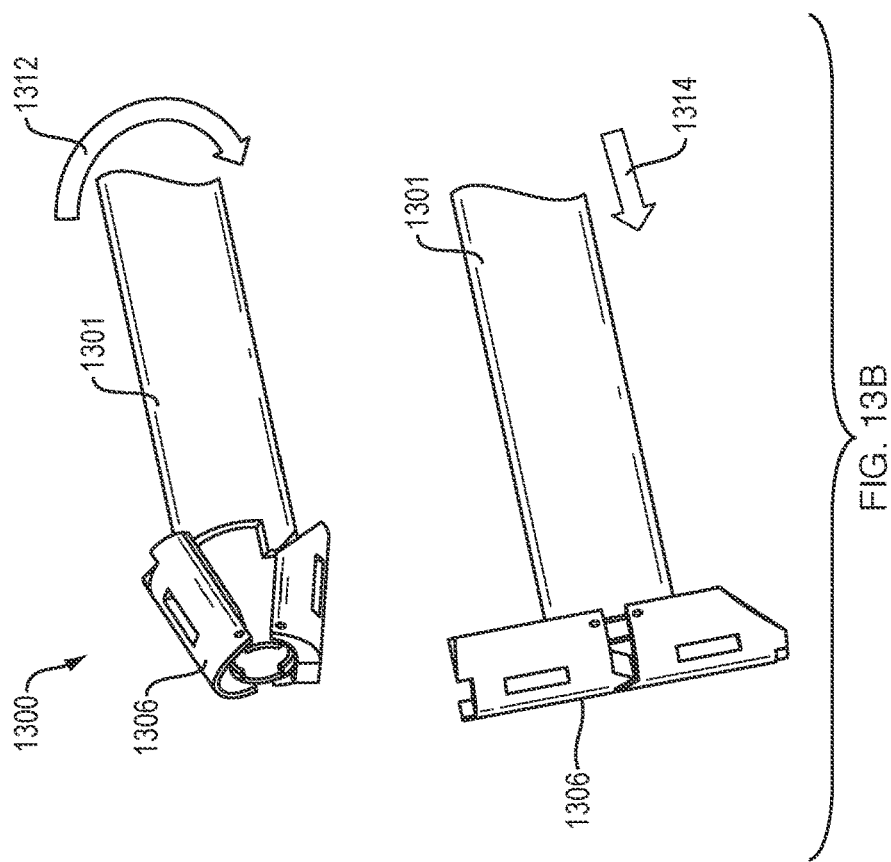
FIGS. 13a and 13b illustrate a seventh alternative embodiment of the retrograde reamer of FIG. 2.
Figure 13A:
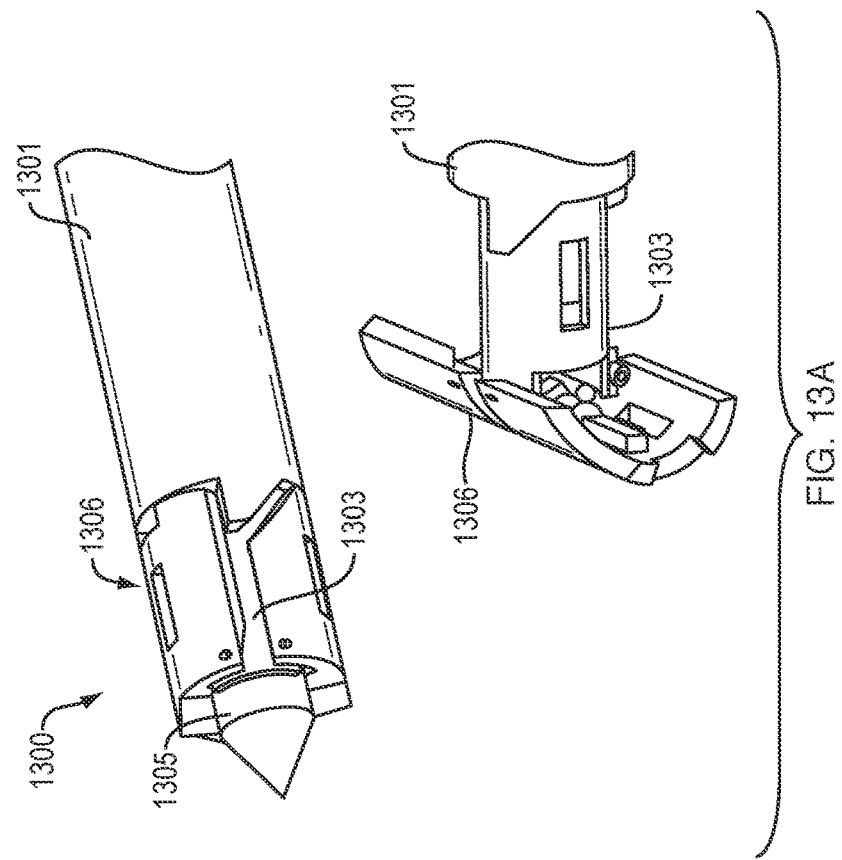

FIGS. 13*a* and 13*b* depict detailed views of the alternative configuration 1300 of the retrograde reamer. As shown in FIGS. 13*a* and 13*b*, the retrograde reamer 1300 includes a shaft 1305 having a distal end with a pointed or sharpened tip, and one or more blades 1306 rotatably attached to a tubular inner shaft 1303 of, for example, a 4.5 mm reamer. During use, the shaft 1305 is initially inserted into the inner shaft 1303, which is disposed within a tubular outer shaft 1301 of the 4.5 mm reamer. To deploy the blades 1306, the shaft 1305 is retracted through the inner shaft 1303, the outer shaft 1301 is rotated to disengage the blades 1306 from the shaft 1301 (see directional arrow 1312), and the outer shaft 1301 is advanced to rotatably position the blades 1306 substantially perpendicular to the respective shafts 1301, 1303 (see directional arrow 1314). To close or collapse the blades 1306, the outer shaft 1301 is retracted to allow the blades 1306 to rotate back against the inner shaft 1303, and the shaft 1305 is advanced into the tubular inner shaft 1303 to maintain the blades 1306 against the shaft 1303. The diameters of tunnels created using the retrograde reamer 1300 can be fixed.

Figure 14:
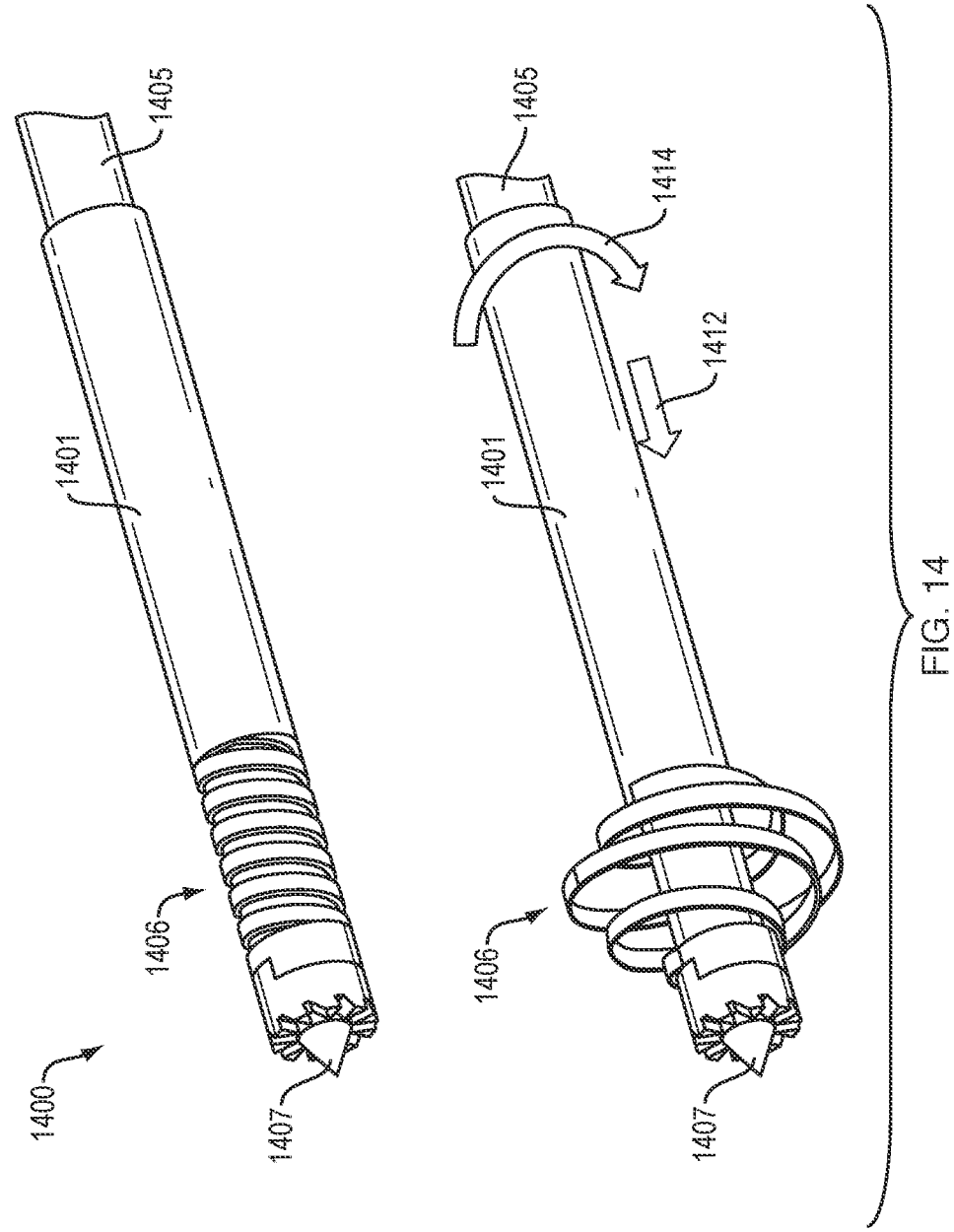
FIG. 14 illustrates an eighth alternative embodiment of the retrograde reamer of FIG. 2.

FIG. 14 depicts a detailed view of the alternative configuration 1400 of the retrograde reamer. As shown in FIG. 14, the retrograde reamer 1400 includes a shaft 1407 having a distal end with a pointed or sharpened tip, and one or more helical blades 1406 (e.g., single or double helix, or interlocking helix members) attached to a tubular outer shaft 1401 of, for example, a 4.5 mm reamer, which also has a tubular inner shaft 1405. During use, the shaft 1407 is inserted into the tubular inner shaft 1405. To deploy the helical blades 1406, the tubular outer shaft 1401 is rotated (see directional arrow 1414) and advanced (see directional arrow 1412) to unwind the helical blades 1406 away from the inner shaft 1405, thereby forming an adjustable cutting diameter. To close or collapse the helical blades 1406, the outer shaft 1401 is rotated in the opposite direction and retracted to wind the helical blades 1406 back against the inner shaft 1405. The diameters of tunnels created using the retrograde reamer 1400 are adjustable based on how far the helical blades 1406 are deployed to form the cutting diameter. Alternatively, the diameters of tunnels created using the retrograde reamer 1400 can be fixed.

FIGS. 15*a*-15*c* depict a further alternative embodiment 1500 of the disclosed retrograde reamer. The retrograde reamer 1500 is an expandable reamer that can be used to perform an anterior cruciate ligament (ACL) repair or reconstruction using the outside in technique. Further, the retrograde reamer 1500 can interface with a suitable aimer to assist the surgeon in the proper placement of the femoral tunnel.

In some embodiments, the retrograde reamer 1500 is cannulated to allow the surgeon to use a standard 2.4 mm guide wire to place the tunnel. As shown in FIGS. 15*a*-15*c*, the retrograde reamer 1500 includes a main shaft 1504, an outer sleeve 1502, and a plurality of cutting members 1506 (e.g., two (2) cutting members). The cutting members 1506 are contained within the main shaft 1504, and swing outward upon activation of the outer sleeve 1502. The outer sleeve 1502 has windows that allow the respective cutting members 1506 to pass therethrough. The cutting members 1506 move via a rotation about a guide pin 1508. The cutting members 1506 have a cam profile to ensure that, while the outer sleeve 1502 applies axial force, the cutting members 1506 swing outward. FIGS. 15*a* and 15*b* depict the retrograde reamer 1500 in a closed or collapsed configuration and an open configuration, respectively.

FIG. 15*c* depicts the open configuration of the retrograde reamer 1500 in greater detail. The retrograde reamer 1500 allows the use of a standard 2.4 mm guide pin. Further, the outer sleeve 1502 is configured to deploy and retract the cutting members 1506. Moreover, the retrograde reamer 1500 can be cannulated to allow deployment and drilling over a guide wire. The cutting members 1506 can also be changed to accommodate all desired sizes (e.g., 6 mm to 13 mm). Advantages of the retrograde reamer 1500 include its capability to have a cannulated configuration, the integral configuration of the cutting members 1506, its capability to be powered via a suitable drill, and its capability to be configured with the dual cutting members 1506, which may allow more accurate tunnel formation.

In an exemplary mode of operation, the guide pin 1508 (e.g., a 2.4 mm guide pin) can be drilled using a suitable aimer. Using the retrograde reamer 1500 in the closed or collapsed configuration (see FIG. 15*a*), a tunnel (e.g., a 4.5 mm tunnel) can then be drilled, from the outside in, through bone into the space of a bone joint. Next, the cutting members 1506 can be activated and deployed by moving the outer sleeve 1502 relative to the main shaft 1504, thereby causing the cutting members 1506 to pass through the windows in the outer sleeve 1502. A tunnel having a desired diameter and depth can then be drilled through the bone in a retrograde fashion, using the cutting members 1506 in their deployed positions. The outer sleeve 1502 and main shaft 1504 can then be advanced back into the space of the bone joint, allowing the cutting members 1506 to be retracted within the main shaft 1504. Finally, the outer sleeve 1502, the main shaft 1504, as well as the cutting members 1506 in their retracted or collapsed positions, can be removed from the surgical site.

Having described the above illustrative embodiments, further modifications to and/or variations of the disclosed surgical instrument may be made, as described below with reference to the following examples. Example 1 is a retrograde reamer for use in surgical procedures that includes a first tubular shaft, at least one second shaft movably disposable within the first tubular shaft, and at least one cutting member movably coupled to one of the first tubular shaft and the second shaft. In response to relative movement of the first tubular shaft and the second shaft, the cutting member is adapted to be displaced from a collapsed position to at least one deployed position, thereby defining at least one cutting diameter.

In Example 2, the subject matter of Example 1 can optionally include features wherein the cutting member is movably coupled to the first tubular shaft.

In Example 3, the subject matter of any one of Examples 1-2 can optionally include features wherein the cutting member is disposed adjacent a distal end of the first tubular shaft, and wherein, in response to relative rotational movement of the first tubular shaft and the second shaft, an externally threaded portion at a distal end of the second shaft is operative to threadingly engage an internally threaded portion at the distal end of the first tubular shaft, thereby causing the distal end of the first tubular shaft to axially move in a proximal direction, and the cutting member to be displaced from the collapsed position to the deployed position.

In Example 4, the subject matter of any one of Examples 1-2 can optionally include features wherein the cutting member includes one or more helical blades, and wherein, in response to relative rotational and axial movement of the first tubular shaft and the second shaft, the helical blades are operative to unwind from the second shaft, thereby displacing the helical blades from the collapsed position to the deployed position.

In Example 5, the subject matter of any one of Examples 1-2 can optionally include features wherein the first tubular shaft has a sidewall, the sidewall including at least one opening therethrough, and wherein the retrograde reamer further includes a flex member operative to movably couple the cutting member to the sidewall of the first tubular shaft substantially opposite the opening in the sidewall, and a deployment member coupled to the cutting member. The deployment member is operative, in response to being pulled distally, to displace the cutting member in a radial fashion from the collapsed position to the deployed position, such that the cutting member passes at least partially through the opening in the sidewall of the first tubular shaft while being displaced to the deployed position.

In Example 6, the subject matter of Example 1 can optionally include features wherein the cutting member is movably coupled to the second shaft.

In Example 7, the subject matter of any one of Examples 1 and 6 can optionally include features wherein, in response to relative axial movement of the first tubular shaft and the second shaft, the cutting member is operative to be displaced from the collapsed position to the deployed position.

In Example 8, the subject matter of any one of Examples 1, 6, and 7 can optionally include at least one wedge member disposed within the first tubular shaft adjacent a distal end of the first tubular shaft, and at least one flex member adapted to movably couple the cutting member to the second shaft. In response to relative axial movement of the first tubular shaft and the second shaft, the cutting member is operative to impinge against the wedge member, thereby causing the flex member to be displaced from a first position substantially parallel to a longitudinal axis of the second shaft to a second off-axis position, and the cutting member to be displaced from the collapsed position to the deployed position.

In Example 9, the subject matter of Example 8 can optionally include features wherein the first tubular shaft has a sidewall with at least one opening formed therethrough, and wherein, in response to the displacement of the flex member, the cutting member is operative to be displaced in a radial fashion from the collapsed position to the deployed position, the cutting member passing at least partially through the opening in the sidewall of the first tubular shaft while being displaced to the deployed position.

In Example 10, the subject matter of any one of Examples 1 and 6 can optionally include features wherein the cutting member is movably coupled at a distal end of the second shaft by a pivot pin.

In Example 11, the subject matter of Example 10 can optionally include features wherein, in response to axial movement of the second shaft in a distal direction, the cutting member is operative to move distally and to rotate about the pivot pin, thereby displacing the cutting member from the collapsed position to the deployed position.

In Example 12, the subject matter of any one of Examples 1, 6, 10, and 11 can optionally include features wherein the first tubular shaft has a sidewall with at least one slot formed therethrough, and wherein, in response to axial movement of the second shaft in a proximal direction, the cutting member is operative to move proximally, thereby causing the cutting member to be placed in the slot in the deployed position.

In Example 13, the subject matter of any one of Examples 1 and 6 can optionally include features wherein the at least one second shaft includes a second tubular shaft, and an internal shaft disposed within the second tubular shaft.

In Example 14, the subject matter of Example 13 can optionally include features wherein the first tubular shaft, the second tubular shaft, and the internal shaft each have a sidewall including at least one opening formed therethrough, and wherein, in response to relative axial movement of the second tubular shaft and the internal shaft, the cutting member is operative to be displaced from the collapsed position to the deployed position, the cutting member passing at least partially through respective sidewall openings of the first tubular shaft, the second tubular shaft, and the internal shaft while being displaced to the deployed position.

In Example 15, the subject matter of any one of Examples 1 and 6 can optionally include features wherein the cutting member is adapted to correspond to a pivotable distal end of the second shaft.

In Example 16, the subject matter of Example 15 can optionally include features wherein, in response to axial movement of the second shaft in a distal direction, the pivotable distal end of the second shaft is operative to rotate, at a pivotable joint, from the collapsed position to the deployed position.

In Example 17, the subject matter of any one of Examples 15-16 can optionally include features wherein the first tubular shaft has a sidewall including at least one slot formed therethrough, and wherein, in response to axial movement of the second shaft in a proximal direction, the pivotable distal end of the second shaft is operative to move proximally, thereby causing the pivotable distal end to be placed in the slot in the deployed position.

In Example 18, the subject matter of any one of Examples 1 and 6 can optionally include features wherein the cutting member has a first cutting member portion and a second cutting member portion, and a flex member interconnecting the first and second cutting member portions.

In Example 19, the subject matter of Example 18 can optionally include features wherein the first tubular shaft has a sidewall including at least one opening formed therethrough, and wherein, in response to axial movement of the second shaft toward a distal end of the first tubular shaft, the flex member is operative to allow the first and second cutting member portions to be displaced from the collapsed position to the deployed position, the first and second cutting member portions passing at least partially through the sidewall opening of the first tubular shaft while being displaced to the deployed position.

In Example 20, the subject matter of any one of Examples 1 and 6 can optionally include features wherein the cutting member is adapted, in the collapsed position, to be selectively engaged with and disengaged from the first tubular shaft, and wherein, in response to relative rotational movement of the first tubular shaft and the second shaft, the cutting member is operative to be disengaged from the first tubular shaft, and to be displaced from the collapsed position to the deployed position.

Example 21 is a method of operating a retrograde reamer in a surgical procedure that includes providing a retrograde reamer, the retrograde reamer including a first tubular shaft, at least one second shaft movably disposable within the first tubular shaft, and at least one cutting member movably coupled to one of the first tubular shaft and the second shaft, performing relative movement of the first tubular shaft and the second shaft, and, in response to the relative movement of the first tubular shaft and the second shaft, displacing the cutting member from a collapsed position to at least one deployed position, thereby defining at least one cutting diameter.

In Example 22, the subject matter of Example 21 can optionally include features wherein the performing of relative movement of the first tubular shaft and the second shaft includes performing relative rotational movement of the first tubular shaft and the second shaft.

In Example 23, the subject matter of any one of Examples 21-22 can optionally include features wherein the performing of relative movement of the first tubular shaft and the second shaft includes performing relative axial movement of the first tubular shaft and the second shaft.

In Example 24, the subject matter of any one of Examples 21-23 can optionally include features wherein the performing of relative movement of the first tubular shaft and the second shaft includes performing relative rotational and axial movement of the first tubular shaft and the second shaft.

In Example 25, the subject matter of any one of Examples 21-24 can optionally include features wherein the retrograde reamer further includes a flex member movably coupling the cutting member to a sidewall of the first tubular shaft at a location substantially opposite an opening in the sidewall, and a deployment member coupled to the cutting member, and wherein the method further includes pulling the deployment member distally, and, in response to the deployment member being pulled distally, displacing the cutting member in a radial fashion from the collapsed position to the deployed position, the cutting member passing at least partially through the opening in the sidewall of the first tubular shaft while being displaced to the deployed position.

It will be appreciated by those of ordinary skill in the art that still further modifications to and variations of the disclosed surgical instrument may be made without departing from the inventive concepts disclosed herein. Accordingly, the invention should not be viewed as limited except as by the scope and spirit of the appended claims.

What is claimed is:

1. A retrograde reamer, comprising:
   a first tubular shaft having a proximal end, a distal end, and a longitudinal axis extending therebetween;
   a second tubular shaft disposed about the proximal end of the first tubular shaft, the second tubular shaft being rotatably and axially moveable relative to the first tubular shaft; and
   at least one cutting member having a proximal end and a distal end, the distal end of the at least one cutting member pivotably coupled to the distal end of the first tubular shaft, the at least one cutting member having an arcuate shape to conform to an outer surface of the first tubular shaft in a closed position such that an outer surface of the at least one cutting member extends in-line with an outer surface of the second tubular shaft;
   wherein a distal end of the second tubular shaft is configured to engage and disengage the proximal end of the at least one cutting member by the rotation and axial movement of the second tubular shaft relative to the first tubular shaft;
   wherein the distal end of the at least one cutting member is configured to pivot about a pivot axis such that, in an open position, the at least one cutting member extends perpendicular to the longitudinal axis, thereby defining at least one cutting diameter; and
   wherein the first tubular shaft is configured to be disposed over a guide wire.

2. The retrograde reamer of claim 1, wherein the first tubular shaft is a 4.5 mm reamer.

3. The retrograde reamer of claim 1, wherein the at least one cutting member is two cutting members.

4. The retrograde reamer of claim 1, wherein the guide wire is a 2.4 mm guide wire.

5. The retrograde reamer of claim 1, wherein the first tubular shaft is configured to drill a first tunnel through bone in a first direction.

6. The retrograde reamer of claim 5, wherein the at least one cutting member is configured to overdrill a second tunnel within the first tunnel through the bone in a second direction opposite the first direction.

7. The retrograde reamer of claim 1, wherein, in the closed position, at least one distally-projecting, member at the distal end of the second tubular shaft engages the proximal end of the at least one cutting member.

8. The retrograde reamer of claim 1, wherein, in the open position, at least one distally-projecting member at the distal end of the second tubular shaft does not engage the proximal end of the at least one cutting member.

9. The retrograde reamer of claim 1, wherein the cutting diameter is between about 6 mm and 13 mm.

* * * * *